United States Patent [19]

Melloh et al.

[11] 4,221,733

[45] Sep. 9, 1980

[54] BETAINES EXHIBITING IMPROVED SKIN-PROTECTING CHARACTERISTICS

[76] Inventors: Wilhelm Melloh, Bergstrasse 7, 6483 Bad Soden-Salmünster, Eckardroth, Fed. Rep. of Germany; Wolfgang Reinisch, Hedone Ballard Close Coombe Hill, Kingston KT 2 7 PG, Surrey, England

[21] Appl. No.: 960,273

[22] Filed: Nov. 13, 1978

[30] Foreign Application Priority Data

Nov. 12, 1977 [DE] Fed. Rep. of Germany ....... 2750731

[51] Int. Cl.$^2$ ............................ C09F 5/00; C11C 3/00; A61K 7/06
[52] U.S. Cl. .................................. 260/404.5; 427/70; 252/117; 252/546; 252/547
[58] Field of Search .................... 260/404.5 Q; 424/70; 252/117, 546, 547

[56] References Cited

U.S. PATENT DOCUMENTS

| | | | |
|---|---|---|---|
| 3,072,690 | 1/1963 | Lee | 260/404.5 |
| 3,225,074 | 12/1965 | Cowen et al. | 260/404.5 |
| 3,328,307 | 6/1967 | Schmitz | 252/106 |
| 3,928,251 | 12/1975 | Bolich et al. | 424/70 |

FOREIGN PATENT DOCUMENTS 1172802  4/1967  Fed. Rep. of Germany ........ 260/404.5

*Primary Examiner*—John F. Niebling
*Attorney, Agent, or Firm*—G. A. Baracka

[57] ABSTRACT

Betaines exhibiting improved skin-protecting characteristics and particularly reduced eye irritation are provided herein. Additionally, improved cleansing, bathing and disinfecting compositions obtained using these betaines are enccmpassed by the present invention.

4 Claims, No Drawings

BETAINES EXHIBITING IMPROVED SKIN-PROTECTING CHARACTERISTICS

BACKGROUND OF THE INVENTION

1. Field of the Invention

This invention relates to improved skin-protecting betaines and to improved cosmetic formulations, such as cleansing and bathing formulations, obtained therewith.

2. Description of the Prior Art

U.S. Pat. No. 3,225,074 shows compounds (betaines) of formula

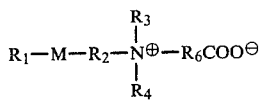

wherein $R_1$ represents long-chain aliphatic hydrocarbon radicals containing from 10–20 carbon atoms, cycloalkyl, aryl, aralkyl, or alkaryl radicals; M represents a bivalent radical such as $-C(=A)-D-$, $-B-C(=A)-$ or $-B-C(=A)-D-$ in which C is carbon and A, B and D are oxygen, sulfur and imino; $R_2$ is an alkylene radical ($-C_mH_{2m}-$) containing from 1 to 24 carbon atoms and preferably 1–12 carbon atoms; $R_3$ and $R_4$ may represent $R_5-M-R_2-$ where $R_5$ is selected from the group consisting of $R_1$ and short-chain aliphatic hydrocarbon radicals, i.e., alkyl and alkenyl, hydroxyalkyl

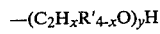

or $-R_6-COOMe$ where x is a whole number from 2 to 4, y is a number from 1 to about 100, R' is methyl, ethyl, tolyl or phenyl, and Me is hydrogen, ammonium or a metal, particularly an alkali metal or an alkaline earth metal; and $R_6$ is an alkylene radical ($-C_mH_{2m}-$) containing from 1 to 12 carbon atoms, and preferably 1 to 6 carbon atoms.

From German Patent No. 11 72 802 a bathing additive is known which comprises a surface active compound of the formula

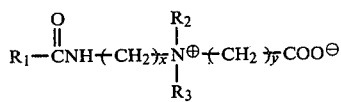

in which $R_1$ is an alkyl radical of a fatty acid with 10 to 18 carbon atoms, $R_2$ and $R_3$ are the same or different alkyl or hydroxyalkyl radicals with 1 to 4 carbon atoms, $x=2$ or 3 and $y=1$, 2, 3, or 4. Compounds of the aforementioned type are recommended as germicidical shampoos. Their non-toxicity on the skin and their unusual low irritation of the eye are particularly recommended. It has been observed, however, that with commercial compounds of this type, such as where $R_1$ is a radical derived from a $C_{12-18}$ fatty acid, $R_2$ and $R_3$ are methyl, $x=3$ and $y=1$, eye compatibility is less than desirable.

SUMMARY OF THE INVENTION

It is an object of this invention, therefore, to provide betaines having improved skin-protecting characteristics and improved cosmetic compositions, such as cleansing, bathing and disinfecting compositions, containing these betaines. In particular, the betaines of this invention and their compositions exhibit less eye irritation and better compatibility with mucous membranes while maintaining the other desired properties.

The improved betaines of this invention correspond to the general formula

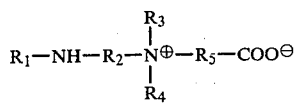

wherein $R_1$ is the acyl radical of ricinoleic acid, $R_2$ and $R_5$ are $C_{1-4}$ alkylene radicals, $R_3$ and $R_4$ are selected from the group $C_{1-4}$ alkyl, $C_{1-3}$ hydroxyalkyl and hydroxypolyethoxy having from 2–20 repeating ethoxy units. Especially useful betaines corresponding to the above formula which exhibit particularly desirable properties have $R_2=C_3$ alkylene, $R_5=$ methylene and $R_3$ and $R_4=$ methyl, ethyl, hydroxyethyl or hydroxypropyl. Advantageously the acyl group $R_1$ can be derived from castor oil fatty acids containing greater than 80% by weight ricinoleic acid. A particularly useful compound of this invention is the betaine form of ricinoylamido-propylen-N-dimethylamino acetic acid.

DETAILED DESCRIPTION

In accordance with this invention improved skin protecting betaines and improved cosmetic compositions, such as cleansing, bathing and disinfecting compositions, containing these betaines are provided. Both the betaines and compositions formulated therewith exhibit significantly reduced eye irritation and better compatability with mucous membranes than the prior art betaines while maintaining the other desired properties.

The present improved betaines correspond to the general formula

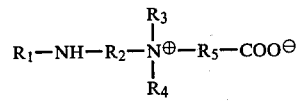

wherein $R_1$ is the acyl radical of ricinoleic acid, $R_2$ and $R_5$ are alkylene radicals, i.e. bivalent hydrocarbon radicals, having 1 to 4 carbon atoms, $R_3$ and $R_4$ are the same or different radicals selected from the group $-C_nH_{2n+1}$ (alkyl) where $n=1$ to 4, the group $-C_nH_{2n}OH$ (hydroxyalkyl) where $n=1$ to 3 or the group $+C_2H_4O+_xH$ (hydroxypolyethoxy) where $x=2$ to 20. Especially useful betaines of the above formula have 3 carbon atoms in the alkylene radical $R_2$, $R_5$ is a methylene ($-CH_2-$) group and the radicals $R_3$ and $R_4$ are methyl, ethyl or or hydroxyalkyl groups having 2 to 3 carbon atoms. Particularly useful is the betain of ricinoylamido-propylen-N-dimethylamino acetic acid.

An essential feature of the novel betaines is that they be derived from ricinoleic acid, i.e. the group $R_1$ is the acyl radical of ricinoleic acid. Without linking the invention to any theory it is believed that the surprisingly good compatability and improved performance of the present betaines is the result of the presence of the hydroxylated unsaturated fatty acyl moiety. In addition to ricinoleic acid, mixtures of fatty acids which are rich in ricinoleic acid can be employed, i.e. mixtures containing at least 50% by weight ricinoleic acid. Fatty acid mixtures obtained from castor oil and which contain greater than 80% by weight ricinoleic acid are especially useful for the preparation of the betaines of this invention. Betaines obtained in this manner exhibit good skin compatibility and, in particular, show good eye compatability and compatability with mucous membranes.

Improved properties are also obtained with formulations containing the above-defined betaines. Compositions containing at least one betaine of the above type and other conventional additives, such as cosmetic compositions including cleansing, bathing and disinfectant formulations, have also been found to be highly advantageous. Primarily these betaine-containing compositions are water-based which will additionally contain other common additives, such as skin-compatible surface active agents, thickening agents, salts, perfumes, dyes and preservatives. Due to their outstanding skin compatability the present betaines can be combined with tensides (tensio-active materials) which have poor skin compatability to improve the skin compatability of these latter compounds. Cleansing and wash compositions formulated using the betaines of this invention find numerous uses in cosmetic applications.

The betaines of this invention are prepared in accordance with methods and procedures known to the art. Detailed explanations of the methods of preparation are available. In general, ricinoleic acid, or a lower alkyl ester (e.g. methyl) of ricinoleic acid, is reacted with a suitable amine and the resulting ricinoylamido compound further reacted with a compound such as monochloroacetic acid to produce the betaine.

Skin compatability of the betaines is tested following the procedure referred to as the "Draize Eye Test" for evaluation of eye lesions according to J. H. Draize in "Appraisal of the Safety of Chemicals in Foods, Drugs and Cosmetics", Association of Food and Drug Officials of the United States (1959). In this test the criterion for the toxicity of a material for the mucous membrane of the eye is the irritation of the eye and its secondary organs.

In the following evaluation employing the Draize Eye Test, data was obtained with the commercial betaine characterized in the introduction, i.e. not derived from ricinoleic acid but rather having an acyl group derived from a conventional (non-hydroxy substituted) $C_{12-18}$ fatty acid, and compared with data obtained with the betaines of this invention. The test was carried out using six test animals with a 5% concentration of the active ingredient in the rabbit eye. Evaluation of eye lesions was made by a point system in which a higher value corresponds to a greater irritation of the eye and the absence of eye irritation is given a value of zero.

The invention is further illustrated with the following examples. All parts and percentages are given in weight unless specifically state otherwise.

EXAMPLE I

Preparation of betaine of ricinoylamido-propylen-N-dimethylamino acetic acid: Ricinoyl methyl ester (310 grams; 1 mole) was heated with 132 grams dimethyl-amino propylamine (30% molar excess) at 150° C. in the presence of phosphoric acid catalyst. The temperature was slowly raised to 190°–195° C. during which time methanol was removed from the reaction mixture. At the completion of the reaction, excess amine was removed under vacuum.

Ricinoylamido-N-dimethylamine (381 grams; 1 mole) obtained by the above procedure was introduced with stirring into a solution made up of 651 grams water, 104 grams monochloroacetic acid (1.1 mole) and 133 grams 33% sodium hydroxide (1.1 mole). The reaction mixture was maintained at 60°–70° C. (pH 7.5–7.8) with agitation. The betaine obtained in this manner produced clear, colorless to slightly yellow, aqueous solutions.

EXAMPLE II

A sanitary solution was prepared by combining 15 parts (40%) ricinoylamido-propylen-N-dimethylamino acetic acid, sodium salt; 10 parts (40%) ricinoleic acid monoethanolamide sulfosuccinate, sodium salt; 5 parts (40%) lauryl alcohol sulfate, triethanolamine salt; and water and with a small amount of perfume agent and preservative to bring the solution to 100 parts. The resulting aqueous (low viscosity) solution had a faint yellow color and exhibited good sanitizing properties.

EXAMPLE III

A mild foaming bathing formulation was prepared by combining 15 parts (40%) ricinoylamido-propylen-N-dimethylamino acetic acid, sodium salt; 10 parts (40%) lauryl alcohol triglycolether sulfosuccinate, sodium salt; 15 parts (40%) lauryl alcohol sulfate, triethanolamine salt; 2 parts diethanolamide of coconut fatty acids; 1.5 parts $NH_4Cl$; and sufficient water to bring the mixture to a total of 100 parts. The above formulation exhibited good foaming and cleansing properties.

EXAMPLE IV

Hair shampoo formulations were prepared employing the betaine of Example I in accordance with the following recipes:

| | DRAIZE EYE TEST | | | | | | | | | |
|---|---|---|---|---|---|---|---|---|---|---|
| | HOURS | | | | DAYS | | | | | |
| | 1 | 2 | 8 | 24 | 1 | 2 | 3 | 4 | 5 | 6 | 7 |
| Commercial Betaine | 13.6 | 16.8 | 15.6 | 20.2 | 20.2 | 17.6 | 6 | 0.8 | 0.8 | 0 | 0 |
| Betaine of This Invention | 9.7 | 11.0 | 9.7 | 2.3 | 2.3 | 0 | 0 | 0 | 0 | 0 | 0 |

The above test results clearly show the substantially better eye compatability obtained with the betaines obtained in accordance with this invention. Eye irritation is much lower at the outset with the present betaines and additionally fades away much faster than with the commercial betaine of the prior art.

| | HAIR SHAMPOO | |
|---|---|---|
| | Dry Hair | Normal and Oily Hair |
| Ricinoylamido-propylen-N-dimethyl-amino acetic acid, sodium salt (40%) | 15 parts | 10 parts |
| Laurylalcohol-triglycolether-sulfosuccinate, sodium salt (40%) | 10 parts | — |
| Laurylalcohol sulfate, triethanolamine salt (40%) | 12 parts | 10 parts |

| | HAIR SHAMPOO | |
|---|---|---|
| | Dry Hair | Normal and Oily Hair |
| Laurylalcohol-triglycolether-sulfate, sodium salt (28%) | — | 20 parts |
| Diethanolamide of the oleic acid | 2 parts | 1.5 parts |
| NH$_4$Cl | 1–2 parts | — |
| NaCl | — | 1–2 parts |

Sufficient water containing a small amount of perfume, dye and preservative was added to each formulation to bring total to 100 parts.

Both medium viscosity formulations had a slight yellow coloration and exhibited good foaming and cleansing characteristics upon application.

EXAMPLE V

A children's and baby shampoo was prepared by combining 15 parts (40%) ricinoylamido-propylen-N-dimethylamino acetic acid, sodium salt; 8 parts (40%) ricinoleic acid monoethanolamide sulfosuccinate, sodium salt; 15 parts (40%) laurylalcohol sulfate, triethanolamine salt; 1–2 parts diethanolamide of oleic acid; 1–2 parts NH$_4$Cl; and sufficient water containing small amount of perfume, dye and preservative to bring the total to 100 parts. The medium viscosity shampoo had a slight yellow coloration.

We claim:

1. Betaines of the formula

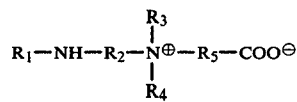

wherein $R_1$ is the acyl radical of ricinoleic acid, $R_2$ and $R_5$ are $C_{1-4}$ alkylene radicals and $R_3$ and $R_4$ are selected from the group $C_{1-4}$ alkyl, $C_{1-3}$ hydroxyalkyl and hydroxypolyethoxy having from 2–20 repeating ethoxy units.

2. The betaine of claim 1 wherein $R_2$ is a $C_3$ alkylene radical, $R_5$ is methylene and $R_3$ and $R_4$ are methyl, ethyl, hydroxyethyl or hydroxypropyl.

3. The betaine of claim 2 wherein $R_3$ is methyl and $R_4$ is methyl.

4. The betaine of claim 1 wherein the acyl group $R_1$ is derived from castor oil fatty acids containing greater than 80% by weight of ricinoleic acid.

* * * * *